US00PP11168P

United States Patent [19]

Heims

[11] Patent Number: Plant 11,168

[45] Date of Patent: Dec. 28, 1999

[54] TIARELLA PLANT NAMED 'NINJA'

[75] Inventor: Dan M. Heims, Portland, Oreg.

[73] Assignee: Terra Nova Nurseries, Inc., Tigard, Oreg.

[21] Appl. No.: 08/982,243

[22] Filed: Dec. 1, 1997

[51] Int. Cl.[6] ..... A01H 5/00

[52] U.S. Cl. ..... Plt./263

[58] Field of Search ..... Plt./68.1, 54.1, Plt./263, 226

[56] References Cited

PUBLICATIONS

Hortus Third: A Concise Dictionary of Plants Cultivated in the United States and Canada, Bailey et al., MacMillan Publishing, New York, p. 1112, 1976.

The New Royal Horticultural Society Dictionary of Gardening, Huxley et al., The Stockton Press, New York, p. 465, 1992.

*Primary Examiner*—Howard J. Locker
*Assistant Examiner*—Anne Marie Grünberg
*Attorney, Agent, or Firm*—Klarquist Sparkman Campbell Leigh & Whinston, LLP

[57] ABSTRACT

A new and distinct hybrid of Tiarella characterized by unique, cut leaves of marked coloration.

2 Drawing Sheets

The present invention relates to a new and distinct hybrid of Tiarella which originated as a single plant from a cross-pollination of a selected seedling of *Tiarella laciniata* and a selected seedling of *Tiarella wherryi* in the Saxifrage family.

The new Tiarella is a result of a controlled cross of the aforementioned plants at Terra Nova Nurseries, Inc., in Portland, Oreg. This hybrid was selected from a large selection of seedlings. Parent plants were retained to observe habit and to compare with their progeny. The parent plants are neither named, patented, or commercially available. The new variety has been reproduced only by asexual propagation (division and tissue culture). Each of the progeny exhibits identical characteristics to the original plant. This plant is characterized by the following:

1. Unique form and foliage shape.

Asexual propagation by division and tissue-culture as done in Canby, Oreg., shows that the foregoing characteristics and distinctions come true to form and are established and transmitted through succeeding propagations.

BRIEF DESCRIPTION OF THE PHOTOGRAPHS

DETAILED PLANT DESCRIPTION

Figure 1:
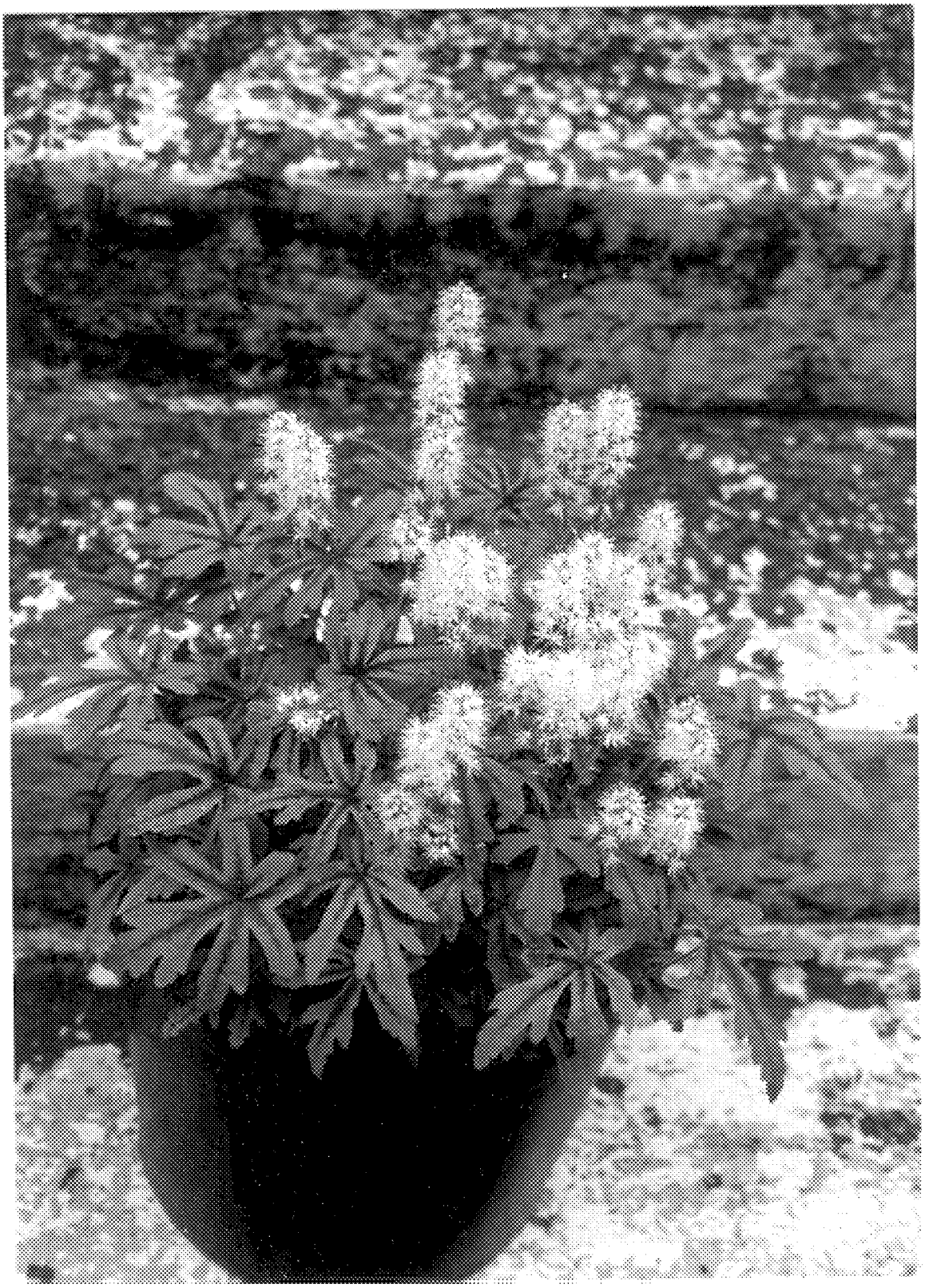
FIG. 1 is a picture of Tiarella 'Ninja' in bloom.
Figure 2:
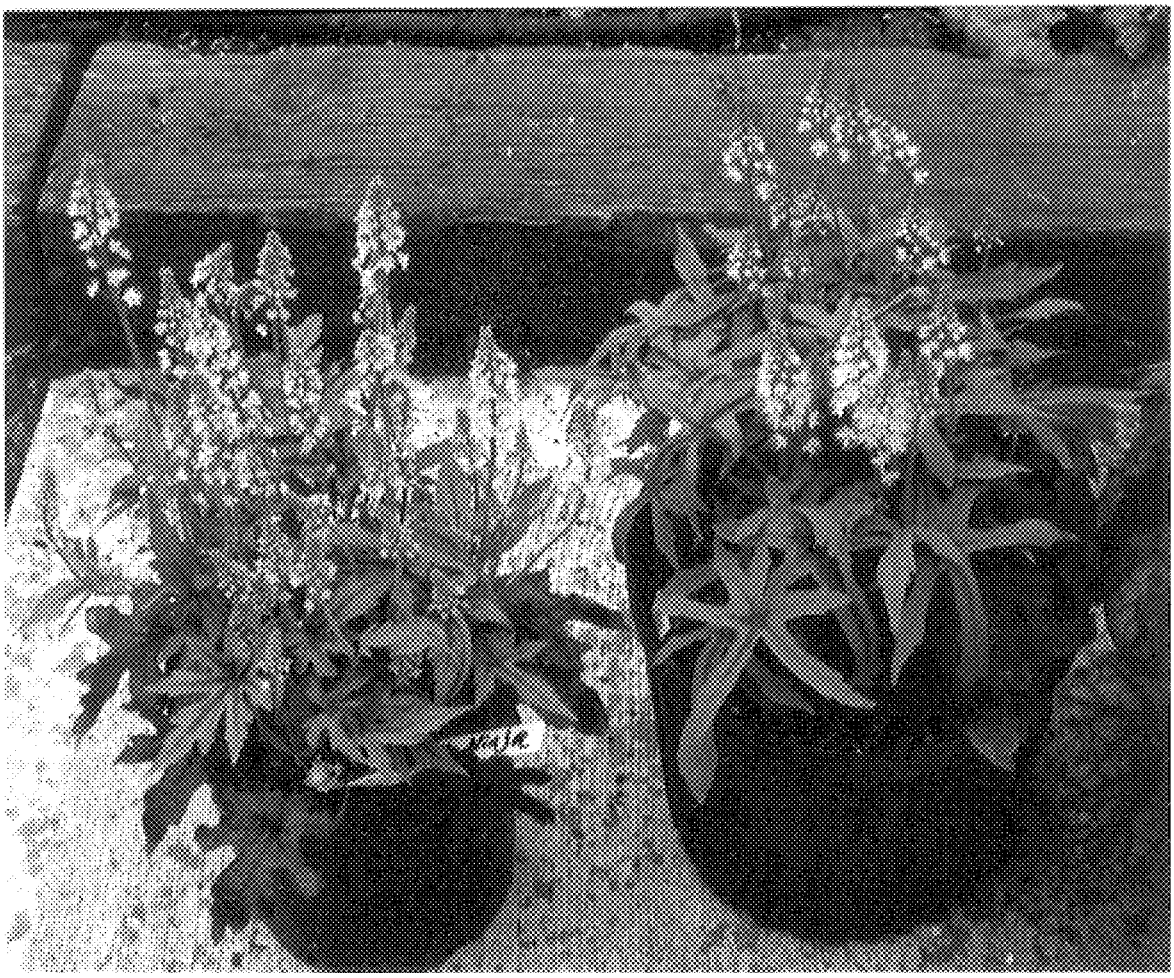
FIG. 2 is a picture of T. 'Ninja' next to T. 'Cygnet', for comparison. Tiarella 'Ninja' is to the left and marked with a white label.

The following is a detailed description of the new Tiarella hybrid based on observations of specimens in Canby, Oreg. The color descriptions are all based on *The Royal Horticultural Society Colour Chart* and The American Rhododendron Society publication: *A CONTRIBUTION TOWARD STANDARDIZATION OF COLOR NAMES IN HORITCULTURE.*

Foliage:

*Type.*—Evergreen, in USDA hardiness zones 5 and above, herbaceous in USDA hardiness zones 3 and 4.
*Shape.*—Palmate, deeply 7-lobed, irregularly toothed.
*Length.*—cm (8.5–9.5).
*Width.*—cm (6.5–7.5).
*Petiole length.*—cm (10–15).

*Margins.*—Incised.
*Apex.*—Acute.
*Base.*—Hastate, slightly imbricate.
*Texture.*—Slightly rugose, light sheen.
*Leaf arrangement.*—Basal clump.
*Venation.*—Reticulate.
*Plant height.*—22 cm in leaf, 36 cm in flower.
*Plant spread.*—(second year) 50 cm.

Flower:

*Petal count.*—5 petals. 5 calyx lobes, 10 stamens, yellow pollen.
*Petal shape.*—Triangular, clawed.
*Flower type.*—Complete, calyx tube campanulate, ovary superior.
*Capsule.*—Beak-like, composed of 2 unequal parts.
*Flower size.*—0.75 cm.
*Flower number.*—35–50 blooms per raceme.
*Blooming habit.*—Simple upright raceme to 25 cm. 45–50 racemes per second-year plant.
*Bloom period.*—May to June. Minor sporadic rebloom in summer and fall. Individual racemes are in color for 2 weeks.
*Fragrance.*—Fragrance is not apparent.
*Fertility.*—Tiarella 'Ninja' is fertile.

Color characteristics:

*Foliage.*—Leaves are sharply discoidal with black along each lobe's central vein and the leaf center.
*Color.*—Spring/Summer upper surface: Two colors of green may be visible on the leaves of the same plant in spring. Coloration is dependent on the maturity of the leaf. Mature leaves show the color R.H.S. 147A (Grey-green Group), and young leaves are R.H.S. 137B (Moderate Olive Green ARS). Winter color upper surface: R.H.S. 187A Greyed Purple (Dark Red ARS). Spring/Summer lower surface: R.H.S. 138A Green Group (Moderate Yellow Green ARS). Spring/Summer new growth and flower stems: R.H.S. 183A Greyed Purple Group (Dark Red ARS). Coloration of the leaf centers on mature leaves is R.H.S. 202A (Black Group).
*Flowers.*—White, shading to pink, pink would be as R.H.S. 36A Red Purple Group. (Light Yellowish Pink ARS). Bud coloration is R.H.S. 186D (greyed Purple Group). Buds are not distinctive from other cultivars.

*Habit.*—This cultivar is not stoloniferous.

DESCRIPTION OF PARENT PLANTS

This Tiarella hybrid has characteristics which make it unique from its parents: a well-marked selection of *Tiarella wherryi* and a selection of *Tiarella laciniata. Tiarella wherryi* is described in Hortus Third as " . . . having more slender racemes and narrower petals" (than *Tiarella cordifolia*) and *Tiarella laciniata*, which is described in Hortus Third as having "rhizomes slender, . . . leaves of 3 leaflets, leaflets divided nearly their full length into irregularly toothed segments". *Tiarella laciniata* also has no contrasting central patch. *Tiarella wherryi* has uncut leaves. Unlike its parents, Tiarella 'Ninja' has both deeply cut leaves which are highly colored, and deep purple winter color.

I claim:

1. A new and distinct hybrid of Tiarella plant substantially as shown and described, characterized by unique, cut leaves of marked coloration.

* * * * *